United States Patent
Menz et al.

(10) Patent No.: US 7,232,587 B2
(45) Date of Patent: Jun. 19, 2007

(54) METHOD FOR THE PASSIVATION OF AN INTRAOCULAR LENS

(75) Inventors: Dirk Henning Menz, Diedorf (DE); Joachim Dresp, Munich (DE); Hans Hoerauf, Sterksdorf (DE)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 10/477,069

(22) PCT Filed: May 8, 2002

(86) PCT No.: PCT/EP02/05039

§ 371 (c)(1),
(2), (4) Date: Apr. 12, 2004

(87) PCT Pub. No.: WO02/093207

PCT Pub. Date: Nov. 21, 2002

(65) Prior Publication Data

US 2004/0166236 A1    Aug. 26, 2004

(30) Foreign Application Priority Data

May 11, 2001    (DE) ................ 101 23 012

(51) Int. Cl.
B05D 5/06    (2006.01)
(52) U.S. Cl. .............. 427/162; 427/164; 427/2.24; 427/430.1; 623/6.11; 623/6.56; 623/6.62
(58) Field of Classification Search .............. 427/2.24, 427/162, 164, 430.1; 623/6.11, 6.56, 6.62
See application file for complete search history.

(56) References Cited

U.S. PATENT DOCUMENTS

| 4,655,770 A |   | 4/1987 | Gupta et al. | ................. 623/1 |
| 5,171,267 A | * | 12/1992 | Ratner et al. | ............. 623/6.57 |
| 5,417,744 A | * | 5/1995 | Gasmena | ...................... 106/2 |
| 5,429,838 A | * | 7/1995 | Mansson et al. | .......... 427/2.24 |
| 5,663,215 A | * | 9/1997 | Milligan | ................... 523/122 |
| 5,945,498 A | * | 8/1999 | Hopken et al. | .............. 528/42 |
| 6,060,123 A | * | 5/2000 | Ogawa | ...................... 427/352 |

FOREIGN PATENT DOCUMENTS

| EP | 0 348 462 B1 * | 5/1994 |
| EP | 0 487 418 B1 | 1/1997 |
| WO | 92/10532 A1 | 6/1992 |

OTHER PUBLICATIONS

English translation of EP 0 487 418 B1; 38 pages; PTO.*

* cited by examiner

Primary Examiner—Alain L. Bashore
(74) Attorney, Agent, or Firm—Vidas, Arrett & Steinkraus

(57) ABSTRACT

The invention includes a method for the passivation of the surface of an intraocular lens, wherein the surface includes Brönsted sites. The intraocular lens is dipped into a solution of a fluoroalkyl silane having the general formula: $R_f$—$(CH_2)_n$—Si—$(O$—$R)_3$. The residue R is selected from the group of H, $CH_3$, $C_2H_5$ and $C_3H_7$ and the fluoroalkyl residue $R_f$ is selected from the series $CF_3(CF_2)_m$, with m=3 to 11 and n=0 to 4. The Brönsted sites on the surface are thereby deactivated by formation of Si—Q—bonds.

9 Claims, No Drawings

METHOD FOR THE PASSIVATION OF AN INTRAOCULAR LENS

CROSS-REFERENCE TO RELATED APPLICATIONS

The present application is a national stage application of PCT/EP02/05039 (WO 02/093207 A1), which claims priority to DB 10123012.5, filed on May 11, 2001, all of which are incorporated herein by reference in their entirety.

BACKGROUND OF THE INVENTION

The present invention relates to a method for the irreversible blocking of reactive Brönsted sites on the surface of an intraocular lens (IOL).

The protection of intraocular lenses against the sticking of substances originating from biological liquids, as well as medical adjuvants has been a demand in ophthalmology for some time. The materials for intraocular lenses are generally made of plastics based on PMMA (polymethylmethacrylate), silicone, and also based on other plastics. Most of these plastic materials have in common that they are selectively partially occupied with reactive sites due to the manufacturing process or the exposition to the environment, respectively. At these sites, substances originating from biological liquids, in particular proteins, are deposited as surface modifying substances in a mechanism which is not yet fully clarified. The interaction of proteins and solid state surfaces is particularly dependent on the functional groups in/at the surface. Among these sites are specifically also Brönsted sites (centres) (e.g. OH, COO), which may be determined for example by reflexion infrared spectroscopy. With the use of IR-microscopy OH-groups have been determined in/at PMMA lenses as well as in/at silicone lenses. Both materials do not show OH-groups in their ideal structure, but—as IR examinations haven proven—varying amounts of OH-groups are present in the real structure.

A further problem of the undesired occupancy of intraocular lenses with other substances is related to the removal of silicone oil adhesions, which can settle on the intraocular lens during a silicone oil tamponade.

Surface coating is a frequently used method to counteract such undesired depositions. With this, a continuous surface film coating is applied in different ways, which forms at least one monomolecular layer, as the following examples show.

U.S. Pat. No. 4,655,770 (briefly '770 in the following) describes the coating of an intraocular lens. The whole ocular lens made of PMMA is covered with a thin inert surface layer, after the surface has been provided with a relatively high concentration of hydroxyl groups by an ozone treatment. As a reagent for the passivation the reaction product of aminoethyl-N-aminopropyl trimethoxysilane and perfluordecanic acid was used in a ratio of 1:3, wherein the coupling of the fluorine compound onto the IOL occurs via a primary process, which calls for several coordinated chemical reactions and is only successful if the surface contains enough OH-groups, and so an ozone pre-treatment is added.

EP-B1-0 487 418 relates to an ophthalmalogical device, the surface of which having been fluorinated in a $CF_4$-plasma, generated from tetrafluorocarbon and sulfur hexafluoride. During fluorination a change of the physical surface properties occurs, due to a complete chemical transformation of the surface regions.

Fluorine coated lenses currently marketed are chemically transformed by a $CF_4$-plasma, compare for example EP-B1-0 487 418. With this, CH-bonds of the polymer are transformed into CF-bonds. As a result, one gets a "teflonised" lens having a low surface energy. With the plasma treatment, the roughness of the surface is decreased simultaneously.

During the plasma treatment several layers of atoms are chemically altered. In contrast to PMMA, silicone also comprises Si—O-bonds. These silicone-oxygen molecule parts may be transformed into the volatile $SiF_4$. The evaporation of $SiF_4$ interferes the formation of non-distorted protective layers or it contributes to an increase in roughness, respectively.

A further possibility is the immersion coating of PMMA lenses with "teflon-AF", compare WO 92/10532. This polymeric perfluoro compound is dissolved in an inert solvent and is then distributed in the form of a thin layer on the surface by means of a immersion (dipping) process. After evaporation of the solvent, the teflon layer sticks to the surface by adhesion.

When using an immersion treatment with teflon-AF the surface of the applied coating must adhesively bind well. OH-groups being present in the silicone, which may be present for example because of the manufacturing conditions, complicate this process because of their hydrophilic nature.

SUMMARY OF THE INVENTION

It is the object of the present invention to provide a method which advantageously passivates and refines the intraocular lens and which generates only minimal changes of the original material, in order to maintain its advantages properties. With this passivation, the occupancies resulting from biological liquids, for example proteins, fats etc., and the deposition and proliferation of cells as well should be prevented in an advantageous manner over the known prior art, and the interactions with medical adjuvants should be prevented also.

The invention includes a method for the passivation of the surface of an intraocular lens, wherein the surface includes Brönsted sites. The intraocular lens is dipped into a solution of a fluoroalkyl silane having the general formula: $R_f$—$(CH_2)_n$—Si—$(O$—$R)_3$. The residue R is selected from the group of H, $CH_3$, $C_2H_5$ and $C_3H_7$ and the fluoroalkyl residue $R_f$ is selected from the series $CF_3(CF_2)_m$, with m=3 to 11 and n=0 to 4. The Brönsted sites on the surface are thereby deactivated by formation of Si—Q—bonds.

DETAILED DESCRIPTION OF THE INVENTION

The inventive method has probably mainly effect because of two mechanisms, namely blockage of eventually present active surface groups, like for example OH, and by the bactericidal, hydrophobic and oleophobic properties, caused by a selective fluorination. Because of the blocking of Brönsted sites, the surface energy is decreased by a reduction of its polar portion, without making a coating or change of the whole surface necessary.

Furthermore, the present invention is based on the finding that it is basically sufficient for a passivation of the intraocular lens to specifically block only those sites by protective groups, which have active surface groups, for example OH or COOH, due to manufacturing or storage conditions.

It has been found that the object formulated above can be solved by a method for blocking reactive Brönsted sites/centres on the surface of an intraocular lens, characterized in that the intraocular lens is dipped into a solution of a fluoroalkyl silane of the general formula

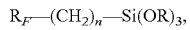
$$R_F—(CH_2)_n—Si(OR)_3,$$

wherein the residue R is selected from the group of H, $CH_3$, $C_2H_5$, $C_3H_7$, and the fluoroalkyl residue $R_F$ is selected from the series $CF_3(CF_2)_m$, with m=3 to 11 and n=0 to 4, whereby the Brönsted sites/centres at the surface are inactivated by formation of Si—O-bonds upon bonding of these protective groups.

The protective groups themselves have bactericidal and oleophobic and hydrophobic properties.

In this connection, the intraocular lens may be a silicone lens or a lens made of polymethyl-methacrylat (PMMA) or acrylics. The solution containing the fluoroalkyl silane is slightly acidified upon application, and contains between 0,5 and 2%, preferably between 0,8 and 1,2% by weight of fluoroalkyl silane(s). Especially preferred is a fluoroalkyl silane, wherein $R_F$=$CF_3(CF_2)_5$, n=2 and R=$CH_2CH_3$. Preferably, the immersion treatment is carried out in a manner that the fluorine content in the surface of the intraocular lens after the treatment is between 2% and 15%. The inventive method, namely the passivation of the surface or regions of the surface, respectively, may be done without any pre-treatment.

For the fluoroalkyl silane the tridecafluoroalkyl triethoxysilane, tradename Dynasilan®, of Hüls AG has proved to be suitable. However, also other fluoroalkyl trialkoxysilanes may be used. The passivation takes place by dipping the lens into an alcoholic and slightly acidified 1% solution of tridecafluoroctyl triethoxysilane and subsequent air drying. Essentially for the passivation are the following reactions:
 a) Hydrolysis of the silane with the formation of highly reactive silanol groups,
 b) rapid reaction of the remaining silanol groups with the OH-groups bonded to the surface, and formation of covalent Si—O-bonds to the surface.

A prerequisite for a successful passivation is thus in any case the existence of OH in/at the surface. These OH-groups, among which also the OH-groups of COOH are, serve as a docking site for the tridecafluoroctyl triethoxysilane. Generally one can state, that all materials comprising OH-groups in/at the surface are suited for such immersion coating. By the immersion coating with DYNASILAN® (tridecafluoroalkyl triethoxysilane), fluoroalkyl residues can be coupled onto the surface of PMMA lenses as well as of silicone lenses. These protective groups are irreversiblychemically fixed to the support and are highly resistant because of their specific structure. Theamount of fluorine in/at the surface after a coating is most probably dependent from the original number of OH-groups in/at the surface, but is lower than the values necessary for a complete coverage.

The proof of effectiveness of the coating of silicone lenses with tridecafluoroctyl triethoxysilane could be shown with AFM (atomic force microscopy). The change of surface roughness of silicone lenses upon coating with DYNASILAN® (tridecafluoroalkyl triethoxysilane) is negligible. Referring to the prior art, for example EP-B 1-0 487 418, it is stated that the types of bonding of fluorine after the coating with tridecafluoroctyl triethoxysilane correspond to the bonding conditions which are determined after a $CF_4$-plasma treatment on the PMMA intraocular lenses. The amount of fluorine in the surface of a tridecafluoroctyl triethoxysilane coating may reach up to about ⅓ of the amount of fluorine which was analyzed after a $CF_4$ plasma treatment (36%). However, it has to be noted that a plasma treatment leads to a complete transformation of the surface, whereas with tridecafluoroctyl triethoxysilane only the chemically active surface regions (OH) are neutralized and irreversibly blocked.

Referring to the proof of effectiveness of the coating with AFM pictures it has to be once again pointed out here, that the change of the surface roughness of IOL due to a coating with DYNASILAN® (tridecafluoroalkyl triethoxysilane) is negligible.

Differences in the AFM pictures are normally caused by the preparation method. However, coated or non-coated lenses reproducibly show a completely different behaviour, which can be shown for example with a BSS (balanced salt solution) rinse. If an uncoated silicone lens is rinsed with BSS, droplets of BSS remain sticking onto the surface, and from these droplets crystals are formed upon evaporation of water. With coated lenses, the BSS solution trickles down despite of the same treatment. The surface remains unchanged when compared to the original state. A crystal formation is completely prevented. In the present invention it could be shown, that also with silicone lenses a surface refinement and passivation could be achieved. With a simple immersion treatment, the surface of silicone and PMMA is equally well modifiable, whereby the defects in the chemical composition of the surface are specifically neutralised. Thus, there is a possibility to passivate and to refine the surface of rigid as well as of flexible IOL.

In contrast to the subject matter of document U.S. Pat. No. 4,655,770, it is possible with the inventive method to passivate even silicone as the lens material instead of PMMA. With the inventive method, different refinements are achieved by a simple dipping procedure. In particular, a surface having low energy is attained which prevents the deposition of cells; an optical refinement is achieved, in that only specific sites are passivated, and all positive properties of the original intraocular lens are maintained. Furthermore, a bactericidal effect is achieved by the compounds coupled to the lens. The surface of the intraocular lens is chemically stabilized. Furthermore, the inventive method may be universally applied to several different materials, because not the material itself, but the Brönsted sites/centres present in the real structure are used for coupling purposes.

A further advantage of the inventive method, particularly in view of the teaching of document '770 is that by a selective blocking of the Brönsted sites/centres being insularly present on the surface of the IOL, a selective refinement on a molecular level occurs. This results in the advantage of a low or negligible and even excludable long term diffusion of physiologically probably critical molecules or aggregates of molecules from the surface regions participating in the chemical reaction. With a complete coverage having a thickness of about 10 Angstrom to about 1 μm, one may conclude that a significant long term diffusion of such substances from the coatings occurs. Furthermore, it has to be remarked, that in the case of silicone lenses an additional layer having a significant thickness disadvantageously influences the mechanical properties of the lens. A silicone lens, in contrast to a PMMA lens, is flexible or can be folded up, respectively, and is introduced in the folded state during the operation, and unfolds itself only after reaching its final position. The high elasticity necessary for this procedure is of course altered by an additional coating completely surrounding the IOL, and which may reach a thickness of 10 μm, and may strongly deteriorate it. Due to the strong mechanical stresses the coatings may develop cracks or may even break.

Additionally, one advantage of the present invention is also that IOL are implants which are used for one of the operations most frequently used and therefore have to be provided in large amounts. Thus, with the inventive method much less amounts of the specific refinement agent are used than for a complete coating of the IOL, in contrast to the method of document '770, also apart from the additional step of the surface pre-treatment, which is not applicable in the present invention.

Furthermore, it has been found that by using the type of fluoroalkyl silane utilised in the present invention the lenses may be provided with bactericidal properties.

For reasons of batch stability and batch conformity, but also for reasons of necessary process validations for the implant manufacture, it is essential not only to minimize the number but also the amount of the adjuvants used, and to restrict the number of the typically necessary production steps to a minimum, which has been achieved with the present invention when compared for example with the method disclosed in document '770.

To summarize, the inventive method is cost effective, does not require a completely reactive surface and does not leave reactive surfaces nor decomposition products of the passivation media.

Thus, with the inventive method there is the great advantage that no surface layer has to be applied, and no surface pre-treatment by etching with ozone or by a chemical priming process has to be done, but instead the OH-groups present in the real structure of the surfaces of the IOL materials are specifically blocked by the fluoroalkyl silane compound, i.e. at the Brönsted centres. With this, a covalent bond is formed between the surface and the fluorosilane. The compounds coupled to the surface even not only block the surface sites responsible for the undesired interactions, but also increase this effect in that by single molecule parts a local hydrophobisation and oleophobisation of the surfaces takes place, which additionally protects against the attack of above-mentioned substances and which are therefore designated as protective groups.

In the following, some examples are provided which illustrate the invention in a non-limiting manner.

EXAMPLES

Example 1

Using IR-microscopy, OH-groups could be determined in PMMA as well as in silicone lenses. By immersion coating with DYNASILAN® (tridecafluoroalkyl triethoxysilane), fluoroalkyl residues could be coupled to the surface of PMMA lenses as well as of silicone lenses. This coating is chemically fixed to the support and is thus highly resistant. The analytical proof of surface changes caused by this dipping procedure was done by XPS measurements. Some results are listed in the table below:

TABLE 1

| Material | Type | Content in the surface after XPS measurements in % | | |
|---|---|---|---|---|
| | | fluorine (F)[1] | oxygen (O)[1] | ratio F/O |
| PMMA | 6791B | 5.2 | 28.1 | 18 |
| PMMA | 88Ti | 11.6 | 25.1 | 46 |

TABLE 1-continued

| Material | Type | Content in the surface after XPS measurements in % | | |
|---|---|---|---|---|
| | | fluorine (F)[1] | oxygen (O)[1] | ratio F/O |
| Silicone | SD-1 | 11.6 | 25.1 | 46 |
| Silicone | C10UV | 3.8 | 31.3 | 12 |

[1]in the bonding state F1s or O1s, repectively.

To demonstrate the effectiveness of the fluorosilane coating with DYNASILAN® (tridecafluoroalkyl triethoxysilane), cell culture experiments with DYNASILAN® (tridecafluoroalkyl triethoxysilane), where carried out. These were growth experiments with rabbit lens epithelial cells.

TABLE 2

The number of cells on IOL types with or without DYNASILAN® (tridecafluoroalkyl triethoxysilane) coating after 72 hours (first row of experiments) are shown in the table below.

| lens | Number of cells after 72 hours | | |
|---|---|---|---|
| | 1 | 2 | 3 |
| p356 + Dyna | 23 | 89 | 91 |
| p356 − Dyna | 275 | 280 | 244 |
| Soflex + Dyna | 44 | 10 | 8 |
| Soflex − Dyna | 37 | 82 | 40 |

TABLE 3

The number of cells on the IOL types with or without DYNASILAN® (tridecafluoroalkyl triethoxysilane) coating after 72 hours (second row of experiments) are shown in the table below.

| lens | Number of cells after 72 hours | | | | | | Average of all experiments |
|---|---|---|---|---|---|---|---|
| | 1 | 2 | 3 | 4 | 5 | 6 | |
| p356 + Dyna | 46 | 34 | 132 | 36 | 96 | 35 | 64.6 |
| p356 − Dyna | 320 | 186 | 110 | 222 | 95 | 333 | 188.1 |
| Soflex − Dyna | 62 | 117 | 182 | 148 | 89 | 130 | 87.8 |
| Soflex − Dyna | 145 | 146 | 193 | 190 | 160 | 101 | 121.6 |

Example 2

42 IOL's made of PMMA, silicone and acrylics, coated with DYNASILAN® (tridecafluoroalkyl triethoxysilane), were incubated in a bacteria suspension (108 KBE/ml) with staph epid. (aerob) and with propionibact. acnes (anaerob). Then the adherent germs were removed by a standardized rinsing method and an ultrasonic treatment from the lenses, incubated after setting up a dilution series on agar plates, and quantified. For both germs, the passivation of the lenses resulted in a decrease of the number of germs, on silicone lenses by 54%, on PMMA lenses by 53% and on acrylic lenses on 31%.

The invention may also be characterized by the following statements:

Statement 1: A method for the passivation of the surface of an intraocular lens, the surface of which comprises Brönsted sites, characterized in that the intraocular lens is dipped into a solution of a fluoroalkyl silane of the general formula

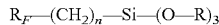

wherein the residue R is selected from the group of H, CH$_3$, C$_2$H$_5$, C$_3$H$_7$, and the fluoroalkyl residue R$_F$ is selected from the series CF$_3$(CF$_2$)$_m$, with m=3 to 11 and n=0 to 4, whereby the Brönsted sites on the surface are deactivated by formation of Si—O-bonds.

Statement 2: A method according to Statement 1, characterized in that the intraocular lens is a silicone lens.

Statement 3: A method according to Statement 1, characterized in that the intraocular lens is a lens made of polyinethylniethacrylate (PMMA) or acrylics.

Statement 4: A method according to anyone of the previous Statements, characterized in that the solution is slightly acidified and comprises between 0.5% by weight and 2% by weight preferably between 0.8% by weight and 1.2% by weight, of the fluoroalkyl silane.

Statement 5: A method according to anyone of the previous Statements, characterized in that R$_F$=CF$_3$(CF$_2$)$_5$, n=2 and R=CH$_2$CH$_3$.

Statement 6: A method according to anyone of the previous Statements, characterized in tat the fluorine content in the surface of the intraocular lens after the immersion treatment is between 2% by weight and 15% by weight.

Statement 7: A method according to anyone of the previous Statements, characterized in that the passivation of the surface is done without pre-treatment.

Statement 8: A method according to anyone of the previous Statements, characterized in that the Brönsted sites are formed by OH-groups.

Statement 9: A method according to anyone of Statements ito 7, characterized in tat the Brönsted sites are formed by CO$_2$-groups.

The invention claimed is:

1. A method of modifying a surface of an intraocular lens, the surface of which comprises Brönsted sites, the method comprising contacting the surface of the lens with a solution of a fluoroalkyl silane of general formula

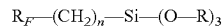

wherein R is selected from the group of H, CH$_3$, C$_2$H$_7$, and R$_F$ is CF$_3$(CF$_2$)$_m$, with m=3 to 11 and n=0 to 4, whereby the fluoroalkyl silane is tethered to the surface by formation of Si—O—bonds at the Brönsted sites on the surface, and the modified surface of the intraocular lens has a fluorine content that is between 2% by weight and 15% by weight, and an oxygen content from 25.1% to 31.3% by weight, as measured by x-ray photoelectron spectroscopy.

2. The method according to claim 1, wherein the intraocular lens is a silicone lens.

3. The method according to claim 1, wherein the intraocular lens is a lens made of polymethylmethacrylate (PMMA) or acrylics.

4. The method according to claim 1, wherein the solution is acidified and comprises between 0.5% by weight and 2% by weight of the fluoroalkyl silane.

5. The method according to claim 1, wherein R$_F$=CF$_3$(CF$_2$)$_5$, n=2 and R=CH$_2$CH$_3$.

6. The method according to claim 1, wherein the Brönsted sites are formed by OH-groups.

7. The method according to claim 1, wherein the Brönsted sites are formed by CO$_2$-groups.

8. The method according to claim 1, wherein the solution is acidified and comprises between 0.8% by weight and 1.2% by weight of the fluoroalkyl silane.

9. The method according to claim 1, wherein the fluorine content is from 3.8% to 11.6% by weight.

* * * * *